United States Patent [19]

Rutsch et al.

[11] Patent Number: 4,824,612
[45] Date of Patent: Apr. 25, 1989

[54] PROCESS FOR OXIDIZING SECONDARY AROMATIC ALCOHOLS

[75] Inventors: Werner Rutsch, Fribourg; Mario Slongo, Tafers, both of Switzerland

[73] Assignee: Ciba-Geigy Corporation, Ardsley, N.Y.

[21] Appl. No.: 129,578

[22] Filed: Dec. 7, 1987

[30] Foreign Application Priority Data

Dec. 15, 1986 [CH] Switzerland .......................... 4987/86

[51] Int. Cl.$^4$ .................................. C07C 145; C07C 00
[52] U.S. Cl. .................................. 260/513.7; 568/315; 568/322; 546/168; 546/340
[58] Field of Search ............. 568/315/322; 260/513.7; 546/168, 340

[56] References Cited

U.S. PATENT DOCUMENTS 3,595,922  7/1971  Manos ................................. 568/315

FOREIGN PATENT DOCUMENTS 53-116302 10/1978  Japan .................................. 568/322
2119362 11/1983  United Kingdom ................. 568/322

OTHER PUBLICATIONS

Albright, J. Org. Chem., vol. 39, pp. 1977–1979 (1974).

*Primary Examiner*—James H. Reamer
*Attorney, Agent, or Firm*—Harry Falber

[57] ABSTRACT

Aromatic ketones or α-diketones can be prepared from the corresponding carbinols by reaction with molar amounts of a sulfonyl chloride in the presence of a base. The corresponding sulfinic acid or salt thereof with the base is formed simultaneously.

10 Claims, No Drawings

PROCESS FOR OXIDIZING SECONDARY AROMATIC ALCOHOLS

The present invention relates to a process for oxidising secondary aromatic alcohols, in particular of the benzhydrol and benzoin type, to the corresponding ketones. In this process, the corresponding benzophenones are formed from the benzhydrols, and the corresponding benzils from the benzoins. Th oxidising agent employed is a sulfonyl chloride, which is reduced to the corresponding sulfinic acid. Hence the process of this invention simultaneously serves the purpose of preparing sulfinic acids from sulfonyl chlorides.

Many processes have already been proposed for oxidising secondary aromatic alcohols to the corresponding ketones. A number of these processes are problematical for environmental reasons, for example the oxidation with nitric acid, in which nitrogen oxides are formed as environmentally harmful by-products. Some processes involve the use of heavy metal catalysts, for example copper or chromate catalysts, which pass into the wastewaters and consequently also become a source of environmental pollution. The process of this invention is carried out under non-corrosive conditions, requires little thermal energy, does not give rise to the formation of any environmentally harmful by-products, and can simultaneously be used for the preparation of sulfinic acids.

The process of this invention can be used for the preparation of aromatic ketones of formula I

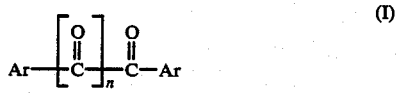

wherein Ar is an aromatic carbocyclic radical of 6 to 14 carbon atoms or an aromatic heterocyclic radical of 4 to 14 carbon atoms, which radical is unsubstituted or substituted by one or more members of the group consisting of halogen, $C_1$-$C_{14}$alkyl, $C_1$-$C_8$alkoxy, phenyl or nitro, and n is 0 or 1, with simultaneous formation of a sulfinic acid of formula R—S(O)—OH, or the alkali metal salt or alkaline earth metal salt thereof, wherein R is $C_1$-$C_8$alkyl, 10-camphoryl, phenyl, naphthyl, or phenyl or naphthyl each substituted by halogen, $C_1$-$C_{14}$alkyl, $C_1$-$C_{12}$alkoxy, phenoxy or phenyl, and comprises reacting a secondary alcohol of formula II

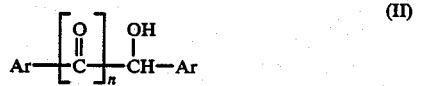

with a sulfonyl chloride of formula R—$SO_2$Cl, in the presence of a base selected from the group consisting of hydroxides, oxides and alcoholates of alkali metals or alkaline earth metals, and in the presence of an organic solvent, in the temperature range from 20° to 150° C., such that not less than 1 mole of $RSO_2Cl$ and not less than 2 equivalents of base are used per mole of the alcohol of formula II.

A carbocyclic radical Ar in formulae I and II is for example phenyl, naphthyl or phenanthryl, preferably phenyl. Examples of substituted carbocyclic radicals Ar are: tolyl, xylyl, 3-ethylphenyl, 4-tertbutylphenyl, 4-octylphenyl, 4-methoxyphenyl, 4-ethoxyphenyl, 4-isopropoxy-2-methylphenyl, 4-chlorophenyl, 4-bromophenyl, 2,4-dichlorophenyl, 4-fluorophenyl, 3-nitrophenyl, 4-biphenyl, 4-nitro-2-naphthyl, 4-chloro-1-naphthyl or hexadecylnaphthyl.

A heterocyclic radical Ar is for example a mononuclear or polynuclear heterocyclic radical containing one or more hetero atoms preferably selected from O, N and S. Such radicals are typically: thienyl, furyl, pyrrolyl, pyridyl, quinolyl, indolyl, carbazolyl or thioxanthyl, and are preferably 2-furyl, 2- or 3-pyridyl or 3-indolyl.

A substituted heterocyclic radical Ar can be in particular an alkylated hetero radical such as methylfuryl, methylpyridyl, dimethylpyridyl, ethylpyridyl or methylquinolyl.

Ar is preferably phenyl or phenyl which is substituted by $C_1$-$C_4$alkyl, $C_1$-$C_4$alkoxy, Cl, Br or $NO_2$.

The process is preferably suitable for the preparation of compounds of formula I, wherein n is 1.

The secondary alcohols of formula II are known compounds and some are commercially available.

The sulfonyl chlorides employed in the process of this invention can be aliphatic, cycloaliphatic or aromatic sulfonyl chlorides. It is preferred to use aromatic sulfonyl chlorides. R as alkyl can be unbranched or branched and is typically: methyl, ethyl, isopropyl, n-butyl, sec-butyl, tert-butyl, octyl, dodecyl or octadecyl. An aromatic radical R is typically phenyl, naphthyl, 4-tolyl, 2-tolyl, 2,4-xylyl, 4-isopropylphenyl, 4-dodecylphenyl, 4-tetradecylphenyl, butylnaphthyl, dodecylnaphthyl, 4-fluorophenyl, 4-chlorophenyl, 3,4-dichlorophenyl, 4-bromophenyl, 4-methoxyphenyl, 4-butoxyphenyl, 4-biphenylyl, 3-nitrophenyl or 4-chloro-3-nitrophenyl. These sulfonyl chlorides are known compounds and can be obtained for example by chlorosulfonation of the appropriate aromatic compound with sulfuryl chloride or with chlorosulfonic acid. It is preferred to use a sulfonyl chloride of formula $RSO_2Cl$, wherein R is methyl, phenyl or naphthyl, or phenyl which is substituted by halogen or $C_1$-$C_{14}$alkyl. The most preferred sulfonyl chloride is toluenesulfonyl chloride or benzenesulfonyl chloride.

Example of suitable bases are: alkali metal hydroxides or alkaline earth metal hydroxides such as NaOH, KOH, LiOH, $Mg(OH)_2$ or $Ba(OH)_2$; alkaline earth metal oxides such as CaO, MgO, SrO, and alkali metal or alkaline earth metal alcoholates such as $NaOCH_3$, $NaOC_2H_2$, $KOC_4H_9$-t, $LiOC_5H_{11}$-t, $NaOCH_2C_4H_9$-t, $NaOC_6H_{13}$-n or $Mg(OC_2H_5)_2$.

Not less than 1 mole of the sulfonyl chloride $RSO_2Cl$ is used per mole of the secondary alcohol of formula II. It is preferred to use 1.0 to 1.5 moles of $RSO_2Cl$.

Not less than 2 equivalents of base are used per mole of the secondary alcohol of formula II. It is preferred to use 2 to 3 equivalents of base.

If NaOH is used as base, the reaction can be illustrated by the following equation:

Examples of suitable organic solvents are hydrocarbons, ethers, cyclic ethers, ketones, esters, halogenated hydrocarbons, dimethylformamide, dimethylsulfoxide, tetramethylenesulfone, hexamethylphosphoric triamide, N,N'-dimethylethylene urea or dimethylacetamide. Hydrocarbons are typically benzene, toluene, xylene or cyclohexane. Ethers and cyclic ethers are typically diethyl ether, diisopropyl ether, dibutyl ether, tetrahydrofuran or dioxane. Ketones are typically acetone, methyl ethyl ketone or methyl isopropyl ketone. Esters are typically ethyl acetate or butyl acetate. Halogenated hydrocarbons are typically tetrachloromethane, methylene chloride, trichloroethylene, tetrachloroethane or chlorobenzene.

The process may be carried out in the presence or absence of water. The presence of water is advantageous if a water-soluble base is used. If an alcoholate is used as base it is advisable to carry out the process under anhydrous conditions. If the process is carried out in the presence of water and a water-immiscible solvent, then it is advisable to add a phase transfer catalyst, for example an ammonium salt, a crown ether, a cryptate, a polyethylene glycol or derivative thereof or a phosphonium salt. It is useful to add such a catalyst in an amount from 0.01 to 10 mol %, based on the compound of formula II. Such a phase transfer catalyst accelerates the reaction and thus shortens the reaction time.

The reaction can be carried out without heating or cooling; but to shorten the reaction time it is advisable to heat to a maximum temperature of 150° C., preferably of 80° C.

To isolate the products, the reaction mixture is preferably converted into an aqueous and an organic phase. The ketone of formula I is present in the organic phase and can be isolated therefrom by concentration and/or crystallisation.

The salt of the sulfinic acid with the base is present in the aqueous phase. It can be isolated as such by salting out or by concentrating the aqueous solution. Alternatively the aqueous solution is acidified with a mineral acid and the free sulfinic acid is isolated by filtration or extraction with an organic solvent. For routine experiments, the content of sulfinic acid in the aqueous phase can be determined by titration with a standardised solution of alkali metal nitrite without isolating the sulfinic acid.

This method of determination is based on the general reaction of sulfinic acids with nitrous acid in accordance with the equation

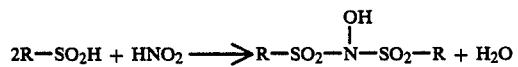

Excess nitrous acid is determined by conventional methods, for example by titration with an acid solution of nitroaniline.

The sulfinic acids as well as the ketones are obtained in this process in a purity that suffices for many utilities. Purification of the isolated ketones can be effected by conventional methods, for example by crystallisation or vacuum distillation. The free sulfinic acids must be isolated and purified with appropriate caution, as these compounds decompose readily and oxidise in air to the corresponding sulfonic acids.

For this last mentioned reason, it is also possible to recycle the sulfinic acids to the sulfonyl chlorides by oxidising the sulfinic acid to the corresponding sulfonic acid, which is then converted into the sulfonyl chloride by reation with a chlorinating agent (e.g. PCl$_5$).

The following Example illustrate the process of this invention, but imply no limitation of the process to these Examples.

EXAMPLE 1

Preparation of benzil and p-toluenesulfinic acid

With stirring, 21.2 g (0.1 mole) of benzoin are added to a mixture of 40 g (0.5 mole) of a 50% aqueous solution of sodium hydroxide and 200 ml of toluene. To the resultant violet suspension are added 1.7 g of tetrabutylammonium bisulfate as phase transfer catalyst, whereupon the suspension turns green. The suspension is heated to 50° C. and, at this temperature, a solution of 20 g (0.105 mole) of p-toluenesulfonyl chloride in 40 ml of toluene is added, with rapid stirring, over the course of 30 to 40 minutes. The resultant yellow emulsion is subsequently stirred for 1 hour at 50° C.

After cooling to room temperature, 200 ml of water are added, whereupon the two phases separate clearly. The organic phase is dried over MgSO$_4$ and concentrated by evaporation under vacuum, affording 20.5 g of benzil as residue in 99% purity (determined by chromatographic analysis), corresponding to a yield of 95% of theory.

A sample of the aqueous phase is acidified with HCl to determine the toluenesulfinic acid present therein and then an excess of 0.1N sodium nitrite solution is added. Excess HNO$_2$ in the resultant white suspension is back-titrated with 0.1N nitroaniline solution until a change in colour to yellow remains constant. The analysis shows a content of 16.6 g of sodium p-toluenesulfinate in the aqueous phase, corresponding to a yield of 93% of theory.

The salt of the sulfinic acid is isolated by saturating the aqueous solution with sodium chloride. The precipitate is isolated by filtration after 1 hour. The filter product is dried in an exsiccator, to give 16.2 g of crude sodium salt of p-toluenesulfinic acid that still contains NaCl.

The free p-toluenesulfinic acid is isolated by acidifying an aqueous solution of the sodium salt with hydrochloric acid. The precipitate is isolated by filtration and, after being dried briefly in an exsiccator, melts at 83°–85° C. (m.p. 85° C. according to the Merck Index). The same product is also obtained by extracting the acid solution with diethyl ether and concentrating the ethereal solution by evaporation.

For confirmation of the structure, 4 g of the crude sulfinic acid are suspended in 100 ml of 1N hydrochloric acid and to the solution is added 0.9 g of NaNO$_2$. The precipitate is isolated by filtration and dried in an exsiccator, to give 4 g of N,N-di-p-toluenesulfonyl hydroxylamine which melts at 125°–126° C. after recrystallisation from ethanol (m.p. 125° C. according to Beilstein XI, 109).

EXAMPLES 2–9

In accordance with the procedure described in Example 1, 0.1 mole of secondary alcohol is reacted with 0.105 mole of sulfonyl chloride and 0.5 equivalent of base, varying the starting components and the solvent. The yield of ketone indicated in Table 1 corresponds to the residue obtained afer concentration of the organic phase, and the purity of the ketone is determined by chromatography. The yield of sulfinic acid is determined by analysis of the aqueous phase (as described in Example 1). The phase transfer catalyst used in Examples 6 and 7 is tetrabutylammonium chloride, and in all other Examples is tetrabutylammonium bisulfate.

TABLE 1

$$R'-C_6H_4-CO-CH(OH)-C_6H_4-R' + RSO_2Cl \longrightarrow R'-C_6H_4-CO-CO-C_6H_4-R' + RSO_2H$$

| Example | R' | R | Solvent | Base | Yield/Purity of ketone | Yield of sulfinic acid |
|---|---|---|---|---|---|---|
| 2 | H | $C_8H_{17}$ | 230 ml of toluene | NaOH | 98%/87% | 53% |
| 3 | H | naphthyl | 240 ml of toluene | NaOH | 97%/92% | 81% |
| 4 | H | " | 200 ml of chlorobenzene | NaOH | 99%/90% | 69% |
| 5 | H | p-tolyl (CH$_3$-C$_6$H$_4$-) | 230 ml of toluene | KOH | 92%/99% | 79% |
| 6 | H | phenyl | 230 ml of toluene | NaOH | 98%/98% | 66% |
| 7 | $CH_3O$ | p-bromophenyl (Br-C$_6$H$_4$-) | 440 ml of toluene | NaOH | 95%/96% | 65% |
| 8 | $CH_3O$ | p-tolyl (CH$_3$-C$_6$H$_4$-) | 390 ml of toluene | NaOH | 95%/95% | 58% |
| 9 | H | p-tolyl (CH$_3$-C$_6$H$_4$-) | 240 ml toluene | Ba(OH)$_2$ | 82%/91% | 85% |

EXAMPLE 10

Preparation of benzophenone 24.7 g (0.22 mole) of potassium tert-butylate are added to a solution of 18.4 g (0.1 mole) of benzhydrol in 160 ml of tetrahydrofuran, and the mixture is heated to 50° C. with stirring. At this temperature, a solution of 21 g (0.12 mole) of p-toluenesulfonyl chloride in 40 ml of tetrahydrofuran is added dropwise over 45 to 60 minutes. The resultant white suspension is stirred for 1 hour, then cooled to room temperature, and 200 ml of water and 200 ml of toluene are added.

The organic phase is dried over MgSO$_4$ and concentrated by evaporation under vacuum, affording as residue 17.8 g of crude benzophenone in 80% purity.

EXAMPLE 11-13

In accordance with the procedure of Example 10, 0.1 mole of carbinol is reacted in the presence of 0.22 mole of potassium tert-butylate in tetrahydrofuran. The results are reported in Table 2.

TABLE 2

| Example | Carbinol | Amount of THF | Sulfonyl chloride | | Yield/Purity of ketone | Yield of sulfinic acid as potassium salt |
|---|---|---|---|---|---|---|
| 11 | benzoin | 240 ml | 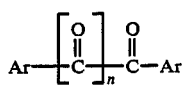 | 0.105 mole | 97%/98% | 85% |
| 12 | benzoin | 230 ml | $CH_3SO_2Cl$ | 0.105 mole | 96%/97% | 57% |
| 13 | α-pyridoin | 440 ml | 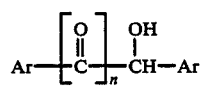 | 0.11 mole | 96%/95% | 67% |

What is claimed is:

1. A process for the preparation of an aromatic ketone of formula I $$Ar\!-\!\left[\!\overset{O}{\underset{\|}{C}}\!\right]_{\!n}\!\overset{O}{\underset{\|}{C}}\!-\!Ar \qquad (I)$$

wherein Ar is an aromatic carbocyclic radical of 6 to 14 carbon atoms or an aromatic heterocyclic radical of 4 to 14 carbon atoms selected from the group consisting of thienyl, furyl, pyrrolyl, pyridyl, quinolyl, indolyl, carbazolyl and thioxanthyl, which radical is unsubstituted or substituted by one or more members of the group consisting of halogen, $C_1$-$C_{14}$alkyl, $C_1$-$C_8$alkoxy, phenyl or nitro, and n is 0 or 1, with simultaneous formation of a sulfinic acid of formula R—S(O)—OH, or the alkali metal salt or alkaline earth metal salt thereof, wherein R is $C_1$-$C_8$alkyl, 10-camphoryl, phenyl, naphthyl, or phenyl or naphthyl each substituted by halogen, $C_1$-$C_{14}$alkyl, $C_1$-$C_{12}$alkoxy, phenoxy or phenyl, which process comprises reacting a secondary alcohol of formula II $$Ar\!-\!\left[\!\overset{O}{\underset{\|}{C}}\!\right]_{\!n}\!\overset{OH}{\underset{|}{CH}}\!-\!Ar \qquad (II)$$

with a sulfonyl chloride of formula R—$SO_2$Cl, in the presence of a base selected from the group consisting of hydroxides, oxides and alcoholates of alkali metals or alkaline earth metals, and in the presence of an organic solvent, in the temperature range from 20° to 150° C., such that not less than 1 mole of $RSO_2Cl$ and not less than 2 equivalents of base are used per mole of the alcohol of formula II.

2. A process according to claim 1, wherein the reaction is carried out in the temperature range from 20° C. to 80° C.

3. A process according to claim 1, wherein in the reaction is carried out under anhydrous conditions in an organic solvent, using an alkali metal alcoholate as base.

4. A process according to claim 1, wherein the reaction is carried out in heterogeneous phase, using an aqueous solution of an alkali metal hydroxide as base.

5. A process according to claim 4, wherein a phase transfer catalyst is added to the reaction mixture.

6. A process according to claim 1, which comprises the use of a sulfonyl chloride of formula $ROS_2Cl$, wherein R is methyl, phenyl or naphthyl, or phenyl which is substituted by halogen or $C_1$-$C_{14}$alkyl.

7. A process according to claim 6, wherein the sulfonyl chloride is toluenesulfonyl chloride or benzenesulfonyl chloride.

8. A process according to claim 1 for the preparation of a ketone of formula I from an alcohol of formula II, wherein Ar in formulae I and II is phenyl or phenyl which is substituted by $C_1$-$C_4$alkyl, $C_1$-$C_4$alkoxy, Cl, Br or $NO_2$.

9. A process according to claim 8, wherein Ar is phenyl.

10. A process according to claim 1 for the preparation of a ketone of formula I from an alcohol of formula II, wherein n in formulae I and II is 1.

* * * * *